US012599713B1

(12) United States Patent
Wang et al.

(10) Patent No.: US 12,599,713 B1
(45) Date of Patent: Apr. 14, 2026

(54) MODULAR PORTABLE ANTI-CHOKING DEVICE WITH ADVANCED SUCTION CONTROL

(71) Applicants: Emerald H.F. Wang, Carmel, IN (US);
 Katherine Y Wang, Carmel, IN (US);
 Chi Wang, Carmel, IN (US)

(72) Inventors: Emerald H.F. Wang, Carmel, IN (US);
 Katherine Y Wang, Carmel, IN (US);
 Chi Wang, Carmel, IN (US)

( * ) Notice: Subject to any disclaimer, the term of this patent is extended or adjusted under 35 U.S.C. 154(b) by 0 days.

(21) Appl. No.: 18/911,945

(22) Filed: Oct. 10, 2024

(51) Int. Cl.
 *A61M 1/00* (2006.01)
(52) U.S. Cl.
 CPC ................ *A61M 1/79* (2021.05); *A61M 1/75* (2021.05); *A61M 2205/07* (2013.01); *A61M 2205/3327* (2013.01); *A61M 2205/3344* (2013.01)
(58) Field of Classification Search
 CPC .......... A61M 1/75; A61M 1/79; A61M 39/22; A61M 39/10; A61M 2205/3344
 See application file for complete search history.

(56) References Cited

U.S. PATENT DOCUMENTS 11,446,460 B1 * 9/2022 Carver ................ A61M 16/208
2024/0066280 A1 * 2/2024 Carver ................ A61M 39/22

* cited by examiner

*Primary Examiner* — Vi X Nguyen

(57) ABSTRACT

A modular portable anti-choking device featuring multiple suction patterns controlled via embedded computing programs is disclosed. The device incorporates an air propeller to generate suction, user-type settings for customizations, and pressure sensors for safety. A dual power supply system enables portability. The compact design makes it suitable for use in various environments including homes, restaurants, and any other settings. Its modular structure allows for easy disassembly, cleaning, and reassembly, making it easy for repeated use. The device ensures effective, safe, adaptable, and reliable operation by dynamically adjusting suction strength based on user-type and real-time sensor data, while minimizing the risk of airway injury caused by excessive suction pressure.

6 Claims, 5 Drawing Sheets

MODULAR PORTABLE ANTI-CHOKING DEVICE WITH ADVANCED SUCTION CONTROL

FIELD OF THE INVENTION

This invention pertains to the field of medical devices, specifically anti-choking apparatuses designed for effectiveness, safety, and portability. It combines reliable electric powered suction, modular disassembly, manual and sensor controls, algorithm controlled suction patterns, and dual power options, making it suitable for any environment, including home, restaurants, and other public spaces.

BACKGROUND OF THE INVENTION

Choking is a critical and life-threatening emergency that requires immediate intervention. It can occur in various environments such as homes, restaurants, and public spaces, often affecting individuals of all ages. According to medical statistics, airway obstructions are a leading cause of unintentional injury-related deaths, especially in young children and the elderly. For example, US National Safety Council reported that in 2022, over 5500 deaths due to choking, ranked the fourth leading causes of unintentional injury related deaths [1]. Traditional methods, such as the Heimlich maneuver, are commonly used to expel blockages from the airway. However, these methods have limitations, particularly in situations where the individual is alone, incapacitated, or where physical strength or technique is inadequate to generate the required force to clear the airway.

In recent years, mechanical suction devices have been introduced as alternatives to manual methods. These devices typically use negative pressure to dislodge the blockage by pulling it away from the airway. However, many existing devices present several drawbacks [2]:

Difficult to operate and unreliable suction: Most of the current devices are manual, requiring both hands applying forces in different directions and generating unreliable suction pressure, sometimes too weak or too strong, depending on the rescuer's skills and strength.

Lack of adaptability: Current devices, manual or automatic, offer only a single, continuous suction pattern/strength, which may not be effective or even increase the risk of injury based on patient characteristics such as age, size, or the nature of the obstruction.

Safety concerns: Devices that generate uncontrolled or excessive negative pressure can cause damage to the airway, especially in vulnerable patients like babies and the elderly. Without adequate safety mechanisms, these devices can collapse the airway or cause soft tissue damage. [2][3]

The present invention addresses these challenges by introducing a modular, portable anti-choking device with embedded control programs that:

Provides multiple suction patterns (e.g., pulse and intermittent suction) to better mimic the natural forces involved in coughing as trying to dislodge obstructions.

Incorporates real-time sensor feedback to dynamically adjust suction strength, ensuring both effectiveness and safety across a wide range of patient types.

Includes safety mechanisms to prevent over-suction and minimize the risk of tissue damage.

The enhanced design offers an effective, reliable, and safe solution for airway obstruction emergencies for all patient types.

DESCRIPTION OF THE RELATED ART

Existing anti-choking devices, whether manual or automatic, have many limitations. With portable manual devices, weak and/or inconsistent suction and cumbersome use are among top reported shortcomings from consumer feedback. Recently commercialized manual devices require the use of both hands, applying forces in different directions (one on mask and one pulling the plunger), and some with small vacuum air chamber creates limited suction, while others with strong suction pose a potential risk of damaging airway tissues. Current portable automatic devices utilize an electric fan or a spring. Insufficient suction power is the most sited drawback by consumers. Additionally, larger electric devices like U.S. Pat. No. 5,609,149 and US 20230372600 offer limited portability due to their bulky size, making them less practical for use outside clinical settings. Our invention addresses these gaps by providing a compact, portable device that offers effective, reliable, and controlled suction with sensor and computing program-controlled pulse and intermittent suction patterns for improved safety. The following are brief descriptions of related prior art patents.

US 20240066280 (Feb. 29, 2024): This invention utilizes manually created vacuum suction but requires both hands pushing (the mask down) and pulling (the plunger) in opposite directions, making it difficult for a single individual to operate effectively and often requires additional personnel to assist the patient. The operation also yields variable suction depending on the rescuer's skills and strength, limiting its effectiveness.

U.S. Ser. No. 11/478,575 (Oct. 25, 2022), U.S. Ser. No. 11/701,462 B2 (Jul. 18, 2023), U.S. Ser. No. 11/759, 591 (Sep. 19, 2023) work in similar manners: they utilize manually created vacuum suction with similar limitations of unreliable suction pressure from too weak to too strong.

US 20230053877 (Feb. 23, 2023): This invention utilizes suction effect created by a mechanical spring. It can be operated by one hand but has one-level suction power.

US 20230372600 (Nov. 23, 2023): This invention utilizes suction effect created by airflow dynamics. It is complicated and bulky.

U.S. Pat. No. 4,934,360 (Jun. 19, 1990): This is a manual resuscitator using suction effects created by springs mechanically. Consumer feedback indicates inadequate suction effects.

U.S. Pat. No. 4,971,053 (Nov. 20, 1990): This is another anti-chocking device utilizing suction effect created by a manually driven piston with a spring, also with one-level power.

U.S. Pat. No. 5,609,149 (Mar. 19, 1997): This invention uses a manually operated plunger to provide the suction effect, which is bulky and offers inconsistent effectiveness.

U.S. Pat. No. 8,876,838 (Nov. 4, 2014): This invention uses compressed fluid for suction but requires additional effort for repeated use.

SUMMARY OF THE INVENTION

The present invention relates to a modular, portable anti-choking device that addresses the limitations of existing devices through advanced suction control and enhanced safety features. The device features a propeller-driven suction mechanism controlled by embedded algorithms, enabling it to provide both pulse and intermittent suction modes that can be adjusted based on patient profiles and real-time sensor feedback. The invention provides a customizable, reliable, and easy-to-use alternative with improved effectiveness and safety to traditional methods and existing devices for use in emergency situations of choking.

Key features of the invention include:

1. Propeller-Driven Suction Mechanism:

At the heart of the device is a high-velocity propeller system that generates the necessary suction to effectively dislodge airway obstructions. The propeller is powered by a motor that is controlled by algorithms to vary the suction patterns according to user settings and real-time sensor feedback. This mechanism ensures adequate, consistent suction while offering adjustability and improved safety.

2. Multiple Suction Patterns:

The device offers multiple suction patterns—pulse suction, intermittent, and hybrid suction—to accommodate different types of obstructions and patient profiles.

Pulse Suction: This mode mimics the natural coughing reflex by applying periodic variations in suction strength. The alternating strong and weak suction strengths create a rocking motion that helps to dislodge tightly lodged obstructions.

Intermittent Suction: This mode provides continuous suction for a preset duration, followed by a brief pause. The pause allows the airway tissues to relax, reducing the risk of damage while ensuring effective clearance of larger obstructions.

Hybrid Suction: In this mode, the suction is applied in short, controlled bursts (pulses), with rests between each set of pulses to create intermittent cycles of activity and rest. This dual-mode operation combines the benefits of pulse and intermittent suction patterns.

3. Control Programs:

The device utilizes embedded control program with computing algorithms to govern the operation of the propeller-driven suction mechanism, adjusting the suction strength dynamically based on user setting and real-time sensor feedback. The device monitors both air pressure and motion in the airway of the device to optimize suction performance and ensure patient safety. The device allows the user to select the suction mode and adjust the suction strength according to the patient's age or size e.g., baby, child, adult.

4. User Interface and Customization:

The device includes intuitive user interface elements that allow the device user to easily switch between suction modes, suction strength level, and patient profiles (e.g., baby, child, adult).

5. Safety Mechanisms:

The device includes integrated safety features, including pressure and motion sensors, to ensure the device operates safely and minimize risks of excessive suction, making the device suitable for use by non-professionals in emergency situations:

Pressure Sensors: Continuously monitor the negative pressure applied during suction to prevent excessive force that could cause airway collapse or tissue damage.

Motion Sensors: Detect movement within the airway and automatically stop suction once the obstruction is dislodged.

Automatic Cut-Off: The device includes a fail-safe mechanism that halts suction immediately if unsafe high pressure levels or leaks are detected, or obstruction is removed.

6. Modular and Portable Design:

The device is constructed with a modular design that allows for quick assembly, disassembly, and cleaning. Its compact and lightweight structure makes it easy to carry and store, making it suitable for use in homes, restaurants, public spaces, and other emergency settings.

7. Dual Power Supply:

The device operates with a dual power system, capable of running on both AC power and rechargeable batteries. This configuration provides versatility, enabling the device to be used in locations without immediate access to electricity, such as outdoor areas or remote locations.

8. Filters:

The device includes two filters to capture debris during the suction process.

In summary, the present invention provides significant improvements over existing anti-choking devices by combining a propeller-driven suction mechanism with advanced control programs, safety features, and a modular design, making it a more effective and safer tool for anti-choking rescuer suitable for all user types, including babies, kids, and adults at homes, restaurants, or any other settings.

DETAILED DESCRIPTION OF THE INVENTION

Figure 1:
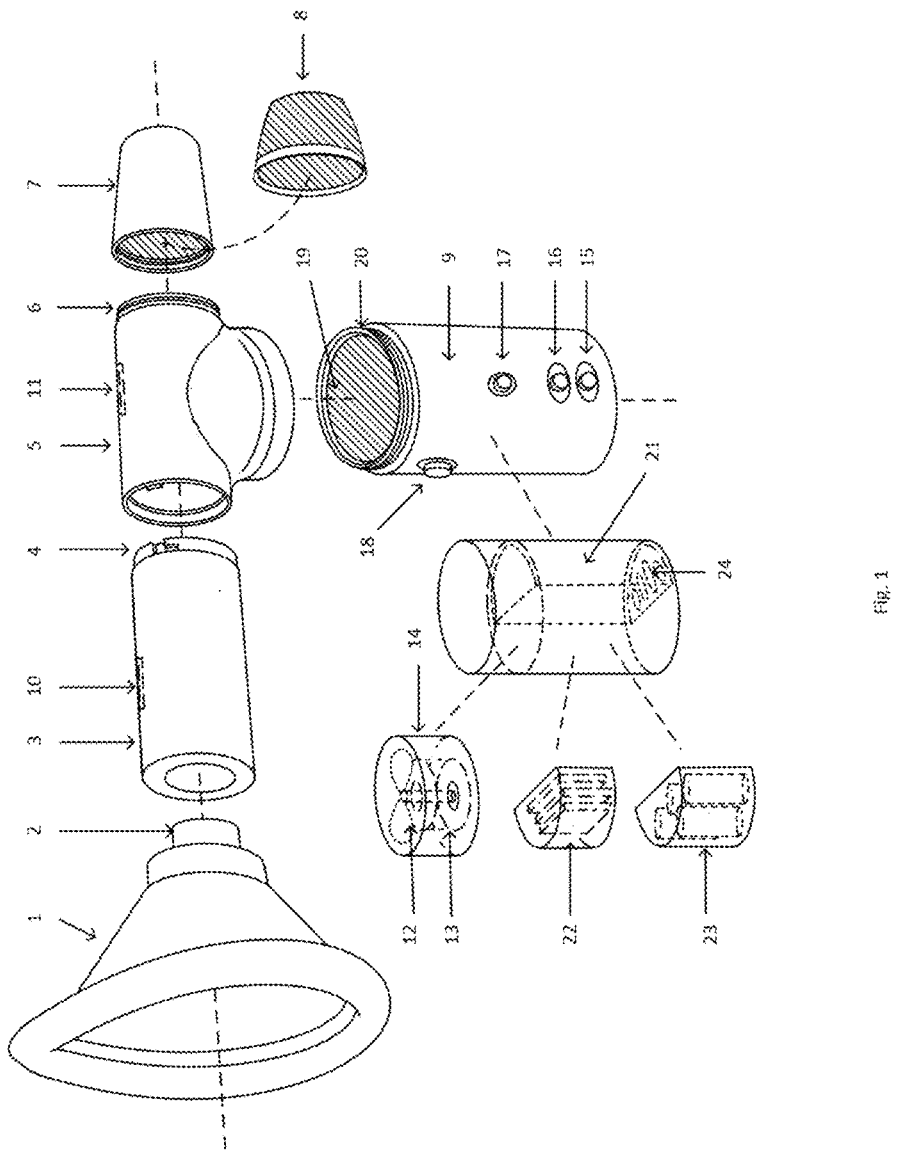
FIG. 1 is a perspective view of key modules and components of an embodiment of the invention.
Figure 2:
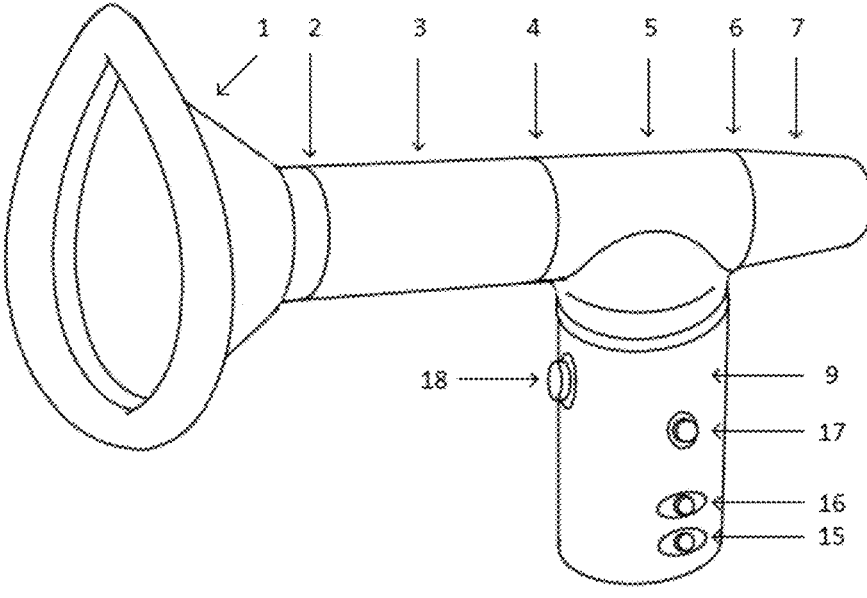
FIG. 2 is a perspective view of the assembled view and an action view of an embodiment of the invention.
Figure 2:
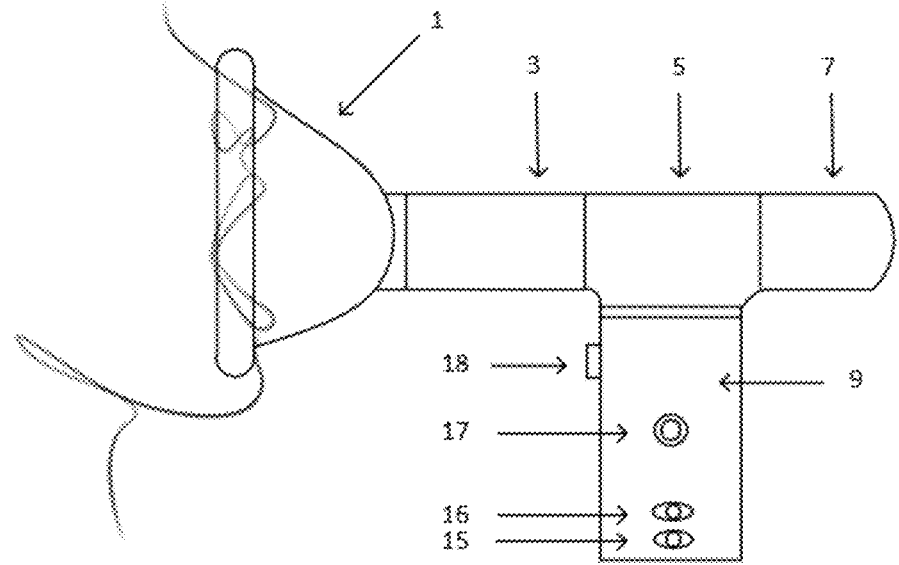
Figure 3:
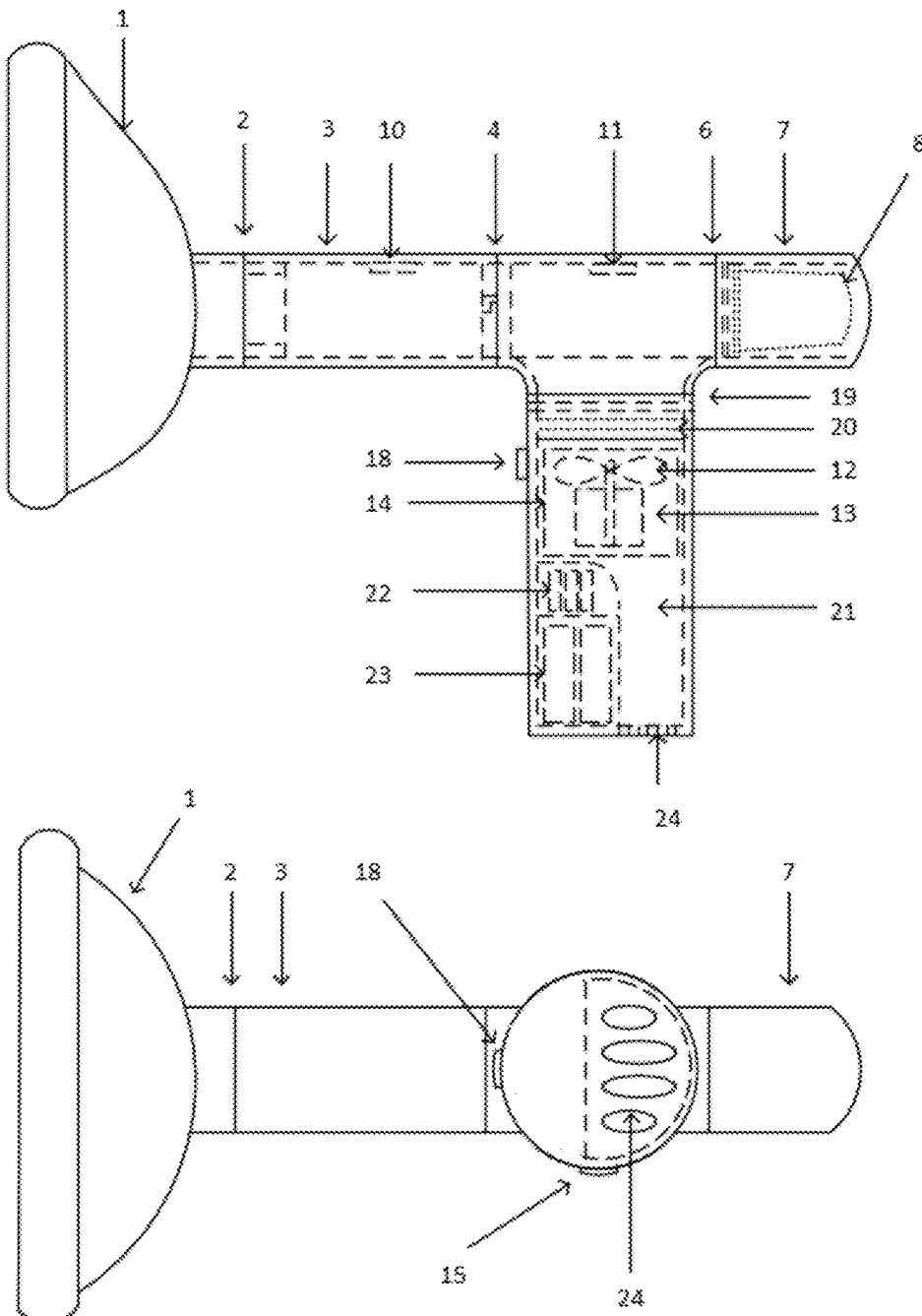
FIG. 3 contains a side section view and a bottom view of an embodiment of the invention.
Figure 4:
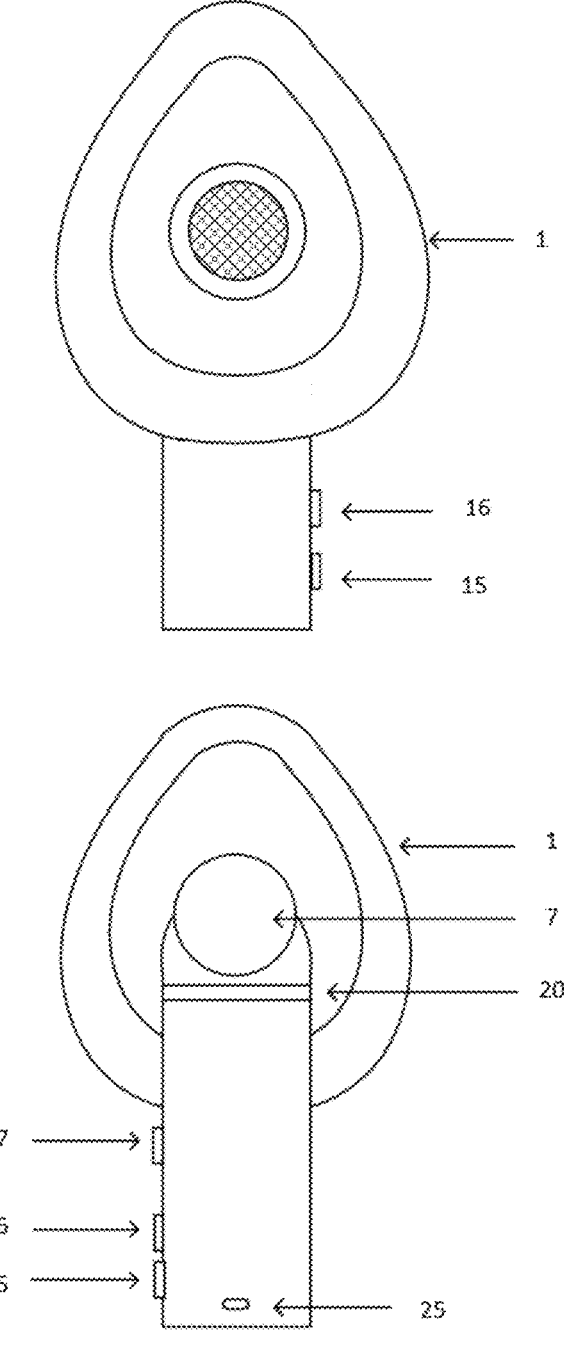
FIG. 4 contains the front view and rear view of an embodiment of the invention.
Figure 5:
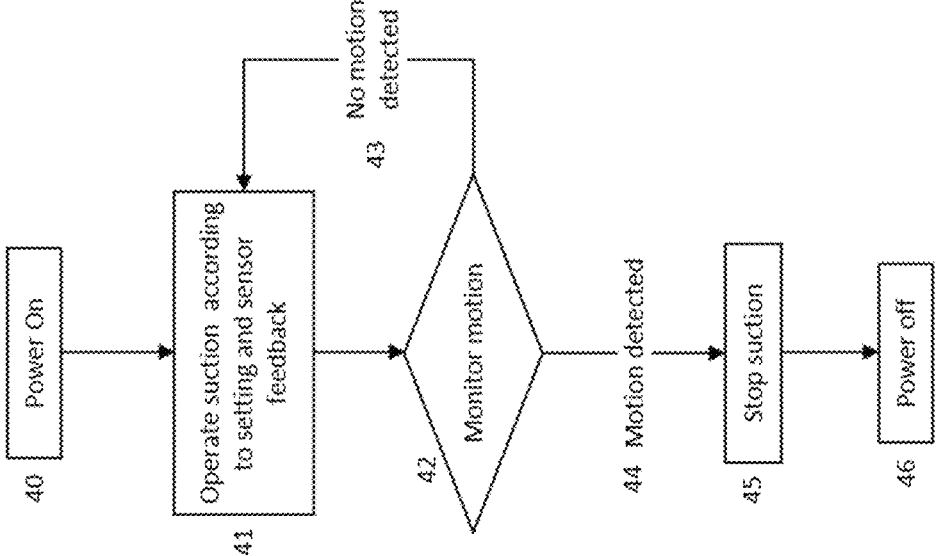
FIG. 5 contains suction workflows of air pressure sensor and motion sensor of an embodiment of the invention.
Figure 5:
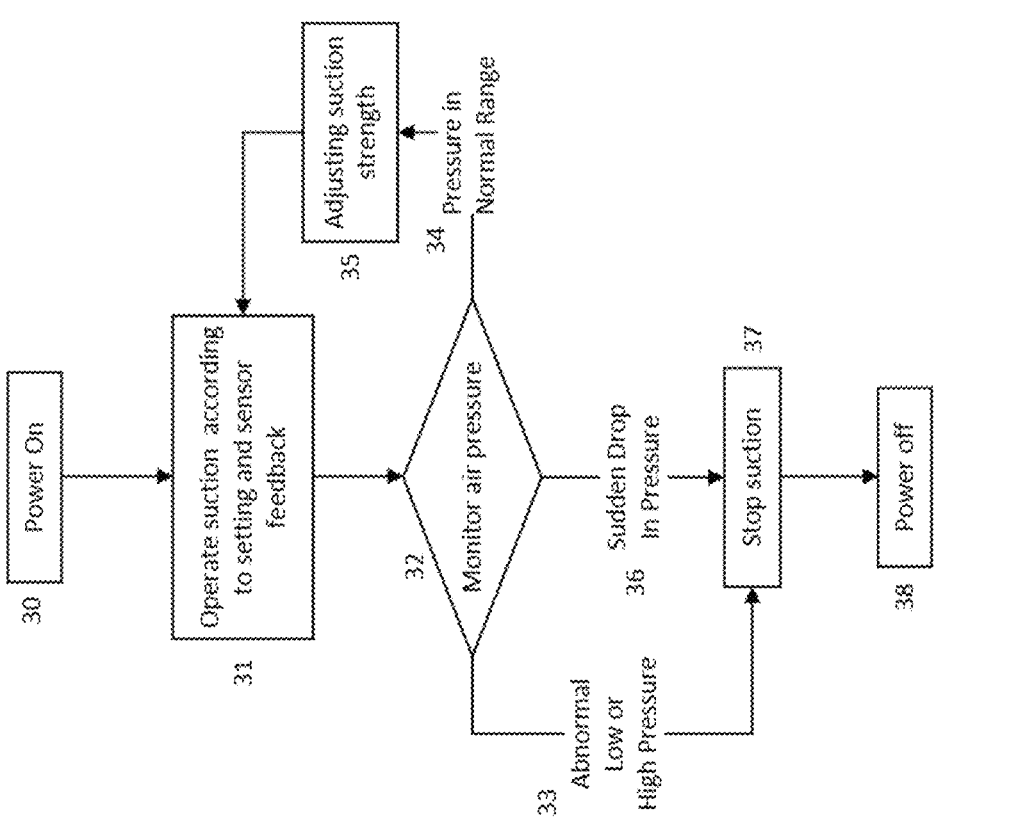

Device Overview:

The anti-choking device comprises multiple innovative features that enhance its functionality, portability, and safety. These include:

Suction Mechanism: The device uses a high-velocity propeller driven by a motor to generate sufficient suction power for airway clearance. The propeller's speed and suction pattern are controlled by embedded algorithms tailored to the patient type and needs.

Multiple Suction Modes: Multiple suction modes are provided:

Pulse Suction: This mode applies varying suction strength over time, controlled by a sinusoidal or triangular wave function. It is particularly effective for dislodging obstructions by creating a rocking or shifting motion of the object.

Intermittent Suction: This mode alternates between continuous suction and brief pauses. The cycle is adjustable based on patient type, with ramp-up and ramp-down times for smooth transitions.

Hybrid Suction: This mode combines both pulsed and intermittent suction functionalities. The suction is applied in short, controlled bursts (pulses), with pauses between each set of pulses to create intermittent cycles of activity and rest.

Control Programs for Enhanced Suction Power and Versatility: The device features advanced control program that dynamically adjusts suction patterns and strength in real time based on sensor feedback. These suction patterns mimicking the natural coughing reflex can deliver more tailored suction power. This flexibility allows the device to handle a wide range of obstruction types with stronger and more stable suction, ensuring a higher success rate in dislodging obstructions safely and efficiently.

Sensor Feedback: Integrated pressure and motion sensors provide real-time monitoring of the device's operation. The feedback from the sensors allows the device to adjust suction operation dynamically for stronger and versatile suction. It ensures that the suction remains within safe limits and stops the device immediately once an obstruction is cleared or if abnormal conditions (e.g., excessive pressure or leaks) are detected.

Dual Power Supply: The device features a dual power option, enabling it to operate either with an AC power source or a rechargeable battery pack. This flexibility allows for uninterrupted operation in any environment.

User Customization: The device provides control options for selecting suction patterns suction strength levels, and patient types, ensuring that the suction is appropriate for different age groups and patient anatomies. The user interface allows easy switching between suction modes, offering adaptability to various emergency situations.

1. Facemask and Air Chambers

In the event of a choking emergency, the facemask (1) is placed securely over the patient's face. The facemask (1) will fit snugly cover the patient's mouth and nose, forming an airtight seal necessary for effective suction. The facemask (1) connects to the air chamber (3) via a push-fit locking mechanism (2), enabling quick attachment and detachment. The air chamber (3) connects to air chamber (5) via a locking mechanism (4). The air flow continues through air chamber (5) then drawn into air chamber (21) inside of the power module (9) by the propeller-motor unit (14), and exits from outlets (24). The propeller-motor unit (14) contains a high-velocity propeller (12) driven by a motor (13) to allow the propeller (12) to create negative suction. Quick-release mechanisms (4), (6), and (20) enable easy assembly, disassembly for cleaning. The facemask utilized in this invention is not a novel component and can be sourced from commercially available providers. Suitable materials for the facemask may include silicone, rubber, or medical-grade plastics, which ensure a secure, airtight seal over the patient's mouth and nose, allowing for effective suction during use. All air chambers (3, 5, 21) and the body of the power module (9) are made from durable materials such as suitable plastic or metal, easy for cleaning and reassembly.

2. Filters

The device uses one or more filters to prevent debris and large particles to enter the power module (9). In an embodiment, a deep pocket shaped filter (8) is placed in the filter cabinet (7). The secondary filter (19) is located at the entrance of the power module (9). Both filters (8) and (19) can be easily mounted and unmounted, allowing for quick cleaning between uses, after the device is disassembled at locking mechanism (6) and (20). Filter (8) is made from flexible materials such as nylon, foam, or other suitable materials that are absorbent, washable/reusable or disposable, designed to absorb/trap small debris and liquid. Filter (19) is made from durable plastic or metal to stop large particles entering the power module (9).

3. Monitoring Sensors

The device uses pressure and motion sensors to monitor suction status and provide feedback to the control system, enabling intelligent management of the suction operation. In an embodiment, sensors (10) and (11) are positioned before and around filters (8) and (19) within the air chambers (3) and (5), continuously tracking air pressure and the movement of extracted objects from the patient's throat. Depending on the embodiment, various sensor types may be employed for monitoring suction status and detecting extracted objects. Motion sensors detect the of objects, while pressure sensors identify changes in pressure caused by the dislodging of obstructions or issues such as facemask leakage or removal. These sensors, used individually or in combination, provide real-time feedback to the control program, allowing for automatic adjustments to suction strength or immediate cessation when the obstruction is cleared or the suction force becomes excessive, ensuring safety and reduce the risk of airway injury.

The sensors utilized in this device, including pressure and motion sensors, are selected from readily available, commercial-grade components to ensure both performance and affordability. These sensors are typically made from high-grade, durable materials such as silicon, ceramics, or polymers, which provide reliable sensitivity and accuracy under varied operating conditions. Additionally, the sensors are designed to withstand sterilization processes and repeated use, maintaining both hygiene and functionality. Pressure sensors are embedded within the air chamber and filter system to detect changes in airflow and obstruction clearance, ensuring real-time feedback to the control circuit. These sensors are widely available in the medical device market and meet rigorous standards for safety and reliability, ensuring the device operates effectively even in emergency scenarios. Careful calibration of the sensors ensures precise measurements of suction force and air pressure, while also preventing overuse or excessive force that could pose risks to the patient's airway.

4. High-Velocity Propeller Module

The propeller-motor module (14), located in the power module (9), is the core component of the suction mechanism. The air propeller (12) is selected from currently available models. The motor (13), which drives the propeller, is a commercially available high-efficiency DC motor, selected for its reliability, compact size, and ability to handle rapid speed changes. The motor is powered by either an AC power source through the charging port (25) or by batteries located in the battery module (23), with power switching managed by an intelligent power management integrated circuit (PMIC) in the control module (22). The motor speed, which dictates both suction strength and suction patterns, is controlled by embedded software in the control circuit. This software dynamically adjusts the motor based on selected patient type (such as baby, child, adult, or elderly), suction range for selected patient type, suction pattern, and real-time feedback from integrated sensors (10), (11). The combination of versatile settings and intelligent control ensures that the propeller-motor module operates effectively and safely, adapting to various patient needs, including children and adults, while maintaining consistent performance.

5. Dual Power Supply

The device features a dual power supply that allows it to operate either via an AC power source connection or a rechargeable battery pack. The power supply components are designed using commercially available, reliable materials, such as lithium-ion for the battery pack and heat-resistant, durable plastics for the power housing. This dual design offers flexibility, ensuring uninterrupted operation regardless of the available power source.

In an embodiment, the power management system including an intelligent power management integrated circuit (PMIC) in the control module (22) with integrated software to manage the power supply:

Automatic Power Source Switching: The power management system will automatically switch between AC power and battery power as needed, ensuring continuous operation. When connected to an AC source, the device prioritizes this power supply, preserving battery life for use when AC power is unavailable.

AC Power Compatibility: When connecting the charging port (25) of the device to an AC outlet, the device operates continuously without drawing power from the battery.

Power Efficiency and Safety: In an embodiment, the power supply design incorporates features such as overcharge protection, short-circuit protection, and automatic shutdown to prevent damage to the device and ensure patient safety. The materials used in the power circuitry and housing are chosen for their ability to withstand repeated charging cycles and high operational loads without degradation.

Rechargeable Battery Pack: The rechargeable battery pack (23) provides a reliable power source during travel or in settings without easy access to electrical outlets.

By integrating a dual power supply system, the device provides maximum flexibility and reliability, making it suitable for various environments, from homes to restaurants.

6. Control Circuits and Embedded Control Programs

The device includes the control module (22) utilizing advanced control circuits that host essential computing programs to manage its operation. The circuits incorporate a Power Management Integrated Circuit (PMIC), which efficiently handles switching between power sources and optimizes battery usage. These circuits also include a motor driver, acting as the interface between the motor and the device's control software, ensuring smooth operation. The control circuits are widely available in the electronics market with established reliability and longevity. The control software, embedded in the circuits, is designed to dynamically manage the suction operation by communicating with sensors and the motor driver. It continuously monitors sensor feedback, such as air pressure and motion within the airway, and adjusts motor speed to modify suction strength in real time. The software is powered by intelligent algorithms, enabling it to automatically alter the suction pattern and strength or stop suction altogether, based on real-time data from the sensors. This adaptability ensures safe and effective operation across different patient types and emergency scenarios.

These control circuits and embedded programs are housed within the control module (22), which is constructed from durable materials like heat-resistant plastics or aluminum to protect the sensitive electronics from external damage or environmental conditions. The circuits are commercially available, off-the-shelf components that meet industry standards for medical devices, ensuring ease of sourcing and replacement if necessary. In different embodiments, the layout and configuration of the control circuits may vary, but they all provide reliable, efficient control over the device's suction operation, prioritizing patient safety and operational effectiveness.

7. User Interface Control Options for Flexibility and Safety

On and Off Switch: When the facemask (1) is correctly positioned and sealed, the user activates the suction function using a power button or a switch. In an embodiment, the user can power the device on using the power control button (18). The user can turn off the suction operation manually by pressing the same button (18). In other embodiments, the device may have other forms of control interfaces for this option.

Patient Type Selector: The device has interface element to let users set patient type, such as babies, children, and adults. Since the safe range of suction strength for different patients varies, this setting makes the device safer and better suits various scenarios. For example, for oropharyngeal or nasopharyngeal suction, medical references suggest safe rage of portable unit for neonates to be between 60-80 mmHg, infants 80-100 mmHg, children 100-120 mmHg, adults 100-150 mmHg. [4] The younger the patient, the risk of damaging soft tissues or airway collapse of damage to mucous membranes may be higher. This patient type option allows the device to be adapted for a wide range of application scenarios and ensuring safety of different types of patients. The control program will automatically adjust maximum suction strength according to this setting. In an embodiment, user can use switch (15) to select patient type. In other embodiments, the device may have other forms of control interfaces for this option.

Suction Strength Selector: The device has interface element to let users select different levels of suction strength. For each type of patient, the device will perform suction with strength within its safe range. For safety, the device may start with suction strength at the lower end of established sage range and gradually increase when needed. For patients of larger size in the same patient type, to save time, user may select to start with a higher strength within the safety range. In an embodiment, user can use interface element (16) to select suction strength. In other embodiments, the device may have other forms of control interfaces for this option.

Suction Pattern Selector: The device has interface element to let users select different suction patterns, including, not limited to, pulse suction, intermittent suction, and hybrid suction. In an embodiment, user uses interface element (17) to select suction pattern. In other embodiments, the device may have other forms of control interfaces for this option:

Pulse Suction: Pulse suction creates suction in bursts with pressure changes in periodic patterns. Pulsed suction is potentially more effective and safer for extracting choking obstructions because it mimics a natural coughing reflexes "pumping" action, which might allow the obstruction to be dislodged more effectively, as opposed to continuous suction. The benefits of pulsed suction include:

Dynamic Pressure Changes: Pulsing creates alternating pressure gradients. This variation could apply intermittent force to the obstruction, loosening it by "rocking" or shifting it slightly with each pulse. This rocking motion may free the obstruction more effectively than a steady pull.

Reduced Risk of Collapse: Continuous suction might create a high vacuum that could cause soft tissues (like the airway walls) to collapse inward or damaging surrounding tissues after the obstruction is removed.

Enhanced Clearance in Fluids: If mucus or liquid is involved along with the obstruction, pulsed suction may help clear these fluids more efficiently, as they can sometimes impede continuous suction by forming a seal around the device's tip.

Higher Maximum Pressure: Pulsed suction may allow for higher maximum pressures without causing damage because it doesn't subject the tissues to constant stress.

Intermittent Suction: Intermittent suction is a cyclical suction pattern, where the device alternates between suction and brief pauses, but without the complex pressure variations in a pulse suction pattern. The benefits of intermittent suction include:

Safety: The pauses between suction allow airway tissues to relax, preventing overexposure to continuous negative pressure, which could lead to tissue damage, airway collapse, or discomfort.

Effectiveness: The brief pauses during intermittent suction can help the body react and reposition the obstruction, allowing a better "grip" on the blockage when suction resumes due to the slight release in pressure.

Versatility: The on-off intervals can be adjusted to different patient needs or types of obstructions, offering a customizable solution without the need for complex pressure control.

Simplicity: This design is easier to implement compared to more complex pulse suction systems because it doesn't require variable suction strength, just timed intervals.

Hybrid Suction: In this mode, the suction is applied in short, controlled bursts (pulses), with pauses between each set of pulses to create intermittent cycles of activity and rest. This dual-mode operation is especially beneficial for applications requiring precision and reduced strain on materials that are sensitive to constant suction or excessive force. The pulse intensity, frequency, and the duration of intermittent pauses can all be adjusted to suit the specific requirements of the task, allowing for a highly customizable suction process. This combined mode ensures optimized efficiency by balancing the need for powerful suction bursts with intervals of reduced or no suction, thus preventing material damage or wear over time.

8. Models for Suction Pattern and Strength

Pulse Suction:

In an embodiment, when the user selected pulse suction pattern, the control program of the embodiment will implement pulse suctions according to selected patient type. To let the suction strength oscillates periodically mimicking the effects of natural coughing reflex, the pulse suction strength is modeled by a sinusoidal function $$S(t) = S_{max} \cdot \sin^2\left(\frac{2\pi t}{T}\right)$$

Where:

S(t) is the suction strength at time t.

$S_{max}$ is the maximum suction strength which depends on the user selected patient type and suction strength level for selected patient type and may vary for a specific design of an embodiment. When integrated with real-time sensor feedback, $S_{max}$ can also be adjusted dynamically within the safe range during the operation.

T is the duration of one full cycle of pulse suction.

In other embodiment, the pulse suction can be further modeled with a time scaling factor that adjusts the frequency or period of suction pulses:

$$S(t) = S_{max} \cdot e^{-\beta t} \cdot \sin^2(2\pi t f(t))$$

Where f(t) is a function that dynamically adjusts the frequency of pulses. For other embodiment, we can let the frequency to increase or decrease over time by setting f(t) as:

$$f(t) = \alpha t + f_0$$

Here:

$f_0$ is the initial frequency of suction pulses.

α controls how quickly the pulse frequency increases or decreases over time

β is the decay factor, controlling how quickly the suction strength diminishes over time.

In other embodiment, if we want more abrupt transitions in suction strength, a triangular wave instead of a sinusoidal wave can be used for the suction strength:

$$S(t) = S_{max} \cdot \left(1 - \left|\frac{2t}{T} - 1\right|\right)$$

Intermittent Suction:

In an embodiment, when the user selected intermittent suction pattern, the control program of the embodiment will implement intermittent suctions according to selected patient type and suction level. Suction is applied continuously for a preset duration, on-time, for example, 3-5 seconds. After this period, the suction briefly stops, for example, off-time, for 1-2 seconds. This on-off cycle repeats for several cycles until the obstruction is cleared or the user stops the device, or the control program stops the device based on sensor feedback.

In an embodiment, the suction strength during the on-time of intermittent suction may follow a trapezoidal pattern, ensuring smooth ramp-up and ramp-down transitions:

$$S(t) = \begin{cases} \dfrac{S_{max}}{T_r} \cdot t, & 0 \le t \le T_r \\ S_{max}, & T_r < t \le T_{on} - T_f \\ S_{max} \cdot \dfrac{T_{on} - t}{T_f}, & T_{on} - T_f < t \le T_{on} \\ 0, & t > T_{on} \end{cases}$$

Where

S(t) is the suction strength at time t.

$S_{max}$ is the maximum suction strength, which varies according to selected patient type, selected suction strength for selected patient type, and design of a specific embodiment. It can also be adjusted dynamically based on real-time sensor feedback.

$T_r$ is the ramp-up time (how long it takes for suction to reach maximum suction strength).

$T_f$ is the ramp-down time (how long it takes for suction to decrease to zero).

$T_{on}$ is the total duration of the on-phase (suction time)

In other embodiment, a simpler approach during the on-time can use a linear model that increases and decreases the suction strength linearly, without the steady-state phase as the trapezoidal model:

$$\begin{cases} S_{max} \cdot \dfrac{t}{T_{on}}, & 0 \le t \le T_{on}/2 \\ S_{max} \cdot \dfrac{T_{on} - t}{\dfrac{T_{on}}{2}}, & T_{on}/2 < t \le T_{on} \\ 0, & t > T_{on} \end{cases}$$

Hybrid Suction:

In this mode, the function for suction strength will be a combination of strength function of pulse suction and intermittent suction. In this dual mode, the suction is applied in short, controlled bursts (pulses), with pauses between each set of pulses to create intermittent cycles of activity and rest. During the on-time, the pulse intensity, frequency will take the form of a pulse suction, and the on-off duration will take the form of intermittent suction. The following is one of such combinations:

$$\begin{cases} S_{max} \cdot e^{-\beta t} \cdot \sin^2(2\pi t f(t)), & 0 \le t \le T_{on} \\ 0, & t > T_{on} \end{cases}$$

Where $S_{max}$, $\beta$, $f(t)$, $T_{on}$ are similarly defined as in pulse and intermittent suctions. Specific form of functions and related parameters will be determined by a specific embodiment.

9. Real-Time Adjustments of Suction Strength

The control program continuously monitors sensor feedback (32), (42) from pressure and motion sensors and adjusts suction strength. When obstruction is cleared, or abnormal pressure is detected, the control program stops operation accordingly.

In an embodiment, maximum strength $S_{max}$ may be dynamically adjusted based on pressure and motion sensor feedback. For example, the $S_{max}$ can be replaced by a function $$SM(t) = S_{base} + K_p \cdot (P_{target} - P(t)) + K_m \cdot M(t)$$

Where:

S(t) is the suction strength at time t, $S_{base}$ is the base suction strength (the minimum suction strength applied). The device starts at the base strength that is safe for selected patient type.

$P_{target}$ is the target pressure (desired negative pressure in the airway) based on the patient type.

P(t) is the real-time pressure reading from the sensor at time t.

M(t) is a motion factor based on motion sensor data (0 if no motion, 1 if motion detected), $K_p$ and $K_m$ are proportional control constants (tuning factors that determine how much the pressure and motion inputs affect the suction strength).

The difference between the target pressure $P_{target}$ and the real-time measured pressure P(t) drives how much the suction strength should be adjusted. If the real-time pressure reading P(t) is lower than the desired value $P_{target}$, it indicates that the suction strength might not be strong enough to dislodge the obstruction. The control program increases S(t) (suction strength) proportionally to the difference between the actual and target pressure values. If P(t) is too high (indicating excessive suction), the algorithm decreases S(t) to avoid airway damage. Above SM(t) can then be used as $S_{max}$ with both pulse suction and intermittent suction. For example, the general strength function $$S(t) = SM(t) \cdot e^{-\beta t} \cdot \sin^2(2\pi t f(t))$$

For a pulse suction can be changed into $$S(t) = (S_{base} + K_p \cdot (P_{target} - P(t)) + K_m \cdot M(t)) \cdot e^{-\beta t} \cdot \sin^2(2\pi t f(t))$$

Similar function can be obtained for the intermittent suction mode.

In an embodiment, such functions will be used in (35) to adjust suction strength based on sensor feedback.

10. Sensor Monitoring and Workflow Logic

The device is equipped with integrated pressure and motion sensors within air chambers continuously monitor the air pressure and motions. In an embodiment, these sensors may be placed as (10) and (11) within the suction chamber (5) and before the filters (8), (19). This real-time feedback allows the device to dynamically adjust the suction operation to ensure proper positioning of the device and safety. An embodiment can implement, not limited to, the following workflows:

In an embodiment, when the device is powered on (30), (40), the control program starts suction operation (31), (41) according to selected patient type and suction pattern. The control program continues monitoring sensor feedback (32), (42). The control program automatically adjusts suction strength and patters in real-time on sensor feedback, ensuring optimal operation and patient safety. The following steps in an embodiment take into account of feedback from both pressure sensors and motion sensors:

Abnormal Air Pressure (33): If the sensors detect low air pressure in the air chambers (3), (5), this indicates that the device is either not correctly positioned on the patient's face or the seal is incomplete. If air pressure in the air chambers (3), (5) exceeds predefined threshold, it indicates risk of excessive force that could cause airway injury. In either case, the control program will stop suction operation (37) to ensure patient safety.

Air pressure within Safe Range (34): When the air pressure in the air chambers (3) and (5) is within the safe range, the control program may adjust suction strength (35) based on sensor feedback and continue suction operation (31).

Sudden Drop in Air Pressure (36): A sudden drop in air pressure in the air chambers (3) and (5) may not exceed the safe range, but it may be an indication of obstruction has been cleared. The control program will immediately cease suction (37) to minimize the risk of injury or discomfort.

No Object Motion Detected (43): If no motion is detected in the air chamber (3) and (5), the system continues suction (41).

Object Motion Detected (44): If motion is detected in the air chamber (3) and (5), the system ceases suction (45) and power off (46) automatically to avoid unnecessary force, minimizing the risk of injury or discomfort.

11. Design and Calibration for Safety and Effectiveness:

As an airway suction device, it is a challenge to be effective and safe. The device's components, including the facemask (1), air chamber (3), (5), (21), and sensors (10), (11), need to be carefully calibrated to accommodate various patient anatomies and usage scenarios. Suction power and the algorithms will be fine-tuned to be strong enough to effectively remove obstructions while maintaining the safety ranges to avoid injury. Calibration settings for suction patterns, timing, duration, and suction levels of an embodiment should be based on experimental data and medical guidelines to ensure safety and optimal performance.

12. Portability and Storage

The device is designed with portability in mind, ensuring it can fit easily into small bags or carrying cases. The modular components, including the facemask (1) and air chambers (3), (5), (21), can be quickly disassembled for easy storage. The lightweight design, combined with detachable parts, ensures the device is easy to carry and ready for use, suitable for parents, caregivers, restaurant owners, or medical professionals in various environments.

The invention claimed is:

1. A modular, portable anti-choking comprising: a facemask configured to form an airtight seal over a patient's mouth and nose: a modular arrangement of air chambers connecting the facemask to a suction mechanism configured to guide airflow: a high-velocity propeller unit configured to generate negative pressure to dislodge airway obstructions: one or more filters configured to capture dislodged debris and prevent it from entering the propeller unit: a dual-power supply system operable with both an AC power source and rechargeable batteries: a control interface elements configured to receive user inputs for patient type, suction strength and suction pattern: sensors configured to monitor air pressure and detect debris motion within the air chambers; and control circuitry embedded with a computing program configured to manage suction operations dynamically based on user selections and real-time sensor feedback; wherein the control circuits store computing programs that is configured to manage suction operations including suction strength and suction patterns for different usage scenarios and safety; and wherein the control circuits is configured to automatically alter the suction pattern and strength or stop suction altogether, based on real-time data from the sensors.

2. The device of claim 1, wherein the control interface is configured to include selection of patient types such as, baby, child, and adult, each mapped to a corresponding safe suction range.

3. The device of claim 1, wherein the suction patterns comprise pulsed suction, intermittent suction, and hybrid suction.

4. The device of claim 1, wherein the suction strength levels comprise low, medium, and high.

5. The device of claim 1, wherein the sensors are placed within one or more of the air chambers and provide real-time feedback to adjust suction power or cease operation.

6. The device of claim 1, wherein the device has a modular design allowing disassembly, cleaning, and reassembly of the facemask, air chambers, propeller unit, and power supply.

* * * * *